(12) United States Patent
Pretz et al.

(10) Patent No.: US 9,815,040 B2
(45) Date of Patent: Nov. 14, 2017

(54) FLUID SOLIDS CONTACTING DEVICE

(71) Applicant: Dow Global Technologies LLC, Midland, MI (US)

(72) Inventors: Matthew T. Pretz, Lake Jackson, TX (US); Don F. Shaw, Denville, NJ (US); Fermin A. Sandoval, Pearland, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/751,424

(22) Filed: Jun. 26, 2015

(65) Prior Publication Data

US 2016/0375419 A1    Dec. 29, 2016

(51) Int. Cl.
*B01J 8/00*    (2006.01)
*B01J 8/18*    (2006.01)
*B01J 19/00*    (2006.01)
*B01J 19/24*    (2006.01)
*B01J 19/30*    (2006.01)
(Continued)

(52) U.S. Cl.
CPC ............... *B01J 8/18* (2013.01); *B01D 3/22* (2013.01); *B01J 8/008* (2013.01); *B01J 8/44* (2013.01); *B01J 19/305* (2013.01); *B01J 19/325* (2013.01); *B01J 2208/0084* (2013.01); *B01J 2208/00884* (2013.01); *B01J 2219/185* (2013.01)

(58) Field of Classification Search
CPC ....... B01J 8/00; B01J 8/18; B01J 19/00; B01J 19/24; B01J 19/32; B01J 19/325; B01J 2208/00796; B01J 2208/00884; B01J 19/30; B01J 19/305; B01J 2219/18; B01J 2219/185; B01J 2219/32–2219/32206; B01J 2219/32213; B01J 2219/32224; B01J 2219/32231; B01J 2219/32237; B01J 2219/32275; B01J 2219/32282; B01J 2219/32286
See application file for complete search history.

(56) References Cited

U.S. PATENT DOCUMENTS 2,472,502 A    6/1949    Tyson
2,481,439 A    9/1949    Ogorzaly
(Continued)

FOREIGN PATENT DOCUMENTS

| CN | 201493095 U | 6/2010 | |
| EP | 0443499 A1 | 8/1991 | |
| GB | 705705 A | * 3/1954 | ............. B01D 53/02 |

OTHER PUBLICATIONS

International Search Report and Written Opinion pertaining to PCT/US2016/039447 dated Sep. 28, 2016.

*Primary Examiner* — Natasha Young
(74) *Attorney, Agent, or Firm* — Dinsmore & Shohl LLP

(57) ABSTRACT

A fluid solids contacting device comprising a vessel; a first grid assembly section which comprises a plurality of horizontal chords spaced horizontally apart from each other and a plurality of grid platforms inserted between the horizontal chords; wherein each horizontal chord comprises a structural member with sufficient mechanical strength to withstand fluidized forces in the vessel; a plurality of chairs attached to an inside surface of the vessel and spaced circumferentially apart to support the structural member; and wherein each structural member is supported on one or more of the plurality of chairs is provided.

8 Claims, 4 Drawing Sheets

(51) Int. Cl.
*B01J 19/32* (2006.01)
*B01D 3/22* (2006.01)
*B01J 8/44* (2006.01)

(56) References Cited

U.S. PATENT DOCUMENTS

| | | |
|---|---|---|
| 2,545,165 A | 3/1951 | Ogorzaly |
| 4,028,442 A | 6/1977 | Eckert |
| 4,615,992 A | 10/1986 | Murphy |
| 5,069,830 A * | 12/1991 | Moore .................. B01J 19/305 |
| | | 261/94 |
| 5,411,710 A | 5/1995 | Iwasyk |
| 5,891,405 A * | 4/1999 | Bianchi .................. B01J 8/008 |
| | | 277/650 |
| 5,910,240 A | 6/1999 | Senior et al. |
| 6,680,030 B2 | 1/2004 | Koebel et al. |
| 7,022,221 B1 | 4/2006 | Hedrick |
| 7,077,997 B1 | 7/2006 | Sandacz |
| 8,669,406 B2 | 3/2014 | Pretz et al. |
| 2009/0214410 A1* | 8/2009 | Blanchard .............. B01J 8/0085 |
| | | 423/437.2 |
| 2013/0252799 A1 | 9/2013 | Johnson, II et al. |
| 2014/0294685 A1 | 10/2014 | Johnson, II et al. |
| 2014/0296603 A1 | 10/2014 | Johnson, II et al. |

\* cited by examiner

FLUID SOLIDS CONTACTING DEVICE

FIELD OF INVENTION

The instant invention relates to a fluid solids contacting device.

BACKGROUND OF THE INVENTION

In fluid bed systems operating a low superficial velocity, gas voidages such as bubbles tend to form which decreases contacting between the gas and the solid phase. In certain situations, internals such as chevrons, subway grating, structured packing or the like are used to break the bubbles and/or prevent formation of bubbles so as to decrease or eliminate the negative impact of inadequate solid/gas phase contact.

In a typical propane dehydrogenation process, internals are desired in the catalyst conditioning zone, the combustor, the reactor stripper, and the reactor itself Subway grating is an excellent choice as it breaks large bubbles into small bubbles while not restricting radial motion in the bed.

At a given gas velocity and flux through a given internal that blocks some of the vessel open area, the bed will flood which will not allow solids to backmix to lower levels and will result in excessive entrainment to the top level of the internal structure. Therefore, the open area and associated gas velocities must be controlled within strict limits of 0.1 ft/s-10 ft/s. Based on the solids flux and volumetric gas flow rate, the minimum open area can be calculated as to avoid flooding. Further, the spacing of internals such as subway grating must be set to avoid the streaming of gas up one side of the structure. Finally, due to the large forces and metal movements arising from high temperatures, a unique mechanical design must be used to account for such movement without causing excessive stress on the vessel or the internals.

SUMMARY OF THE INVENTION

In one embodiment, the instant invention provides fluid solids contacting device comprising a vessel; a first grid assembly section which comprises a plurality of horizontal chords spaced horizontally apart from each other and a plurality of grid platforms inserted between the horizontal chords; wherein each horizontal chord comprises a structural member with sufficient mechanical strength to withstand fluidized forces in the vessel; a plurality of chairs attached to an inside surface of the vessel and spaced circumferentially apart to support the structural member; and wherein each structural member is supported on one or more of the plurality of chairs.

BRIEF DESCRIPTION OF THE DRAWINGS

For the purpose of illustrating the invention, there is shown in the drawings a form that is exemplary; it being understood, however, that this invention is not limited to the precise arrangements and instrumentalities shown.

DETAILED DESCRIPTION OF THE INVENTION

Figure 1:
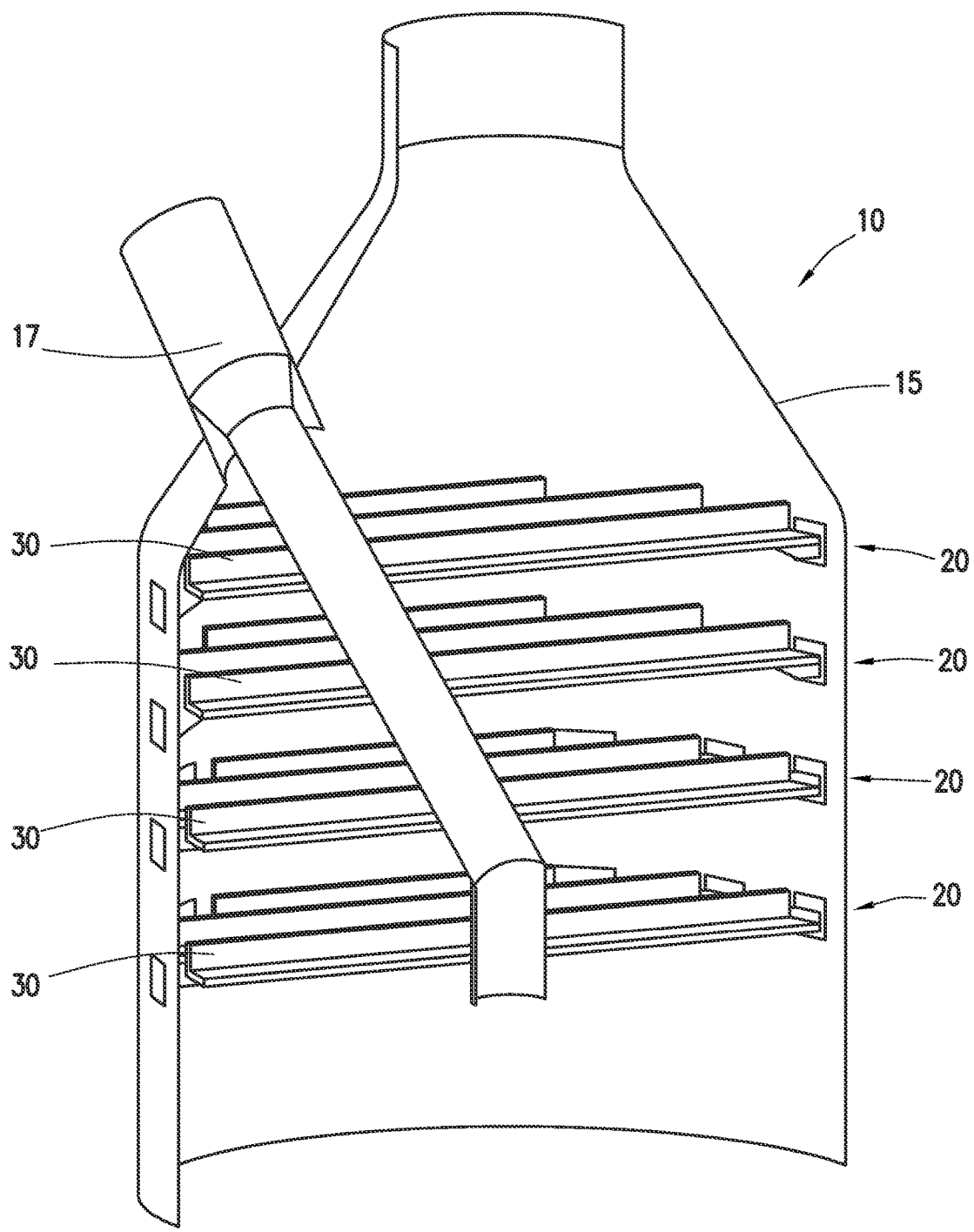
FIG. 1 is a cut-away longitudinal schematic of a first embodiment of a fluid solids contacting device.
Figure 2:
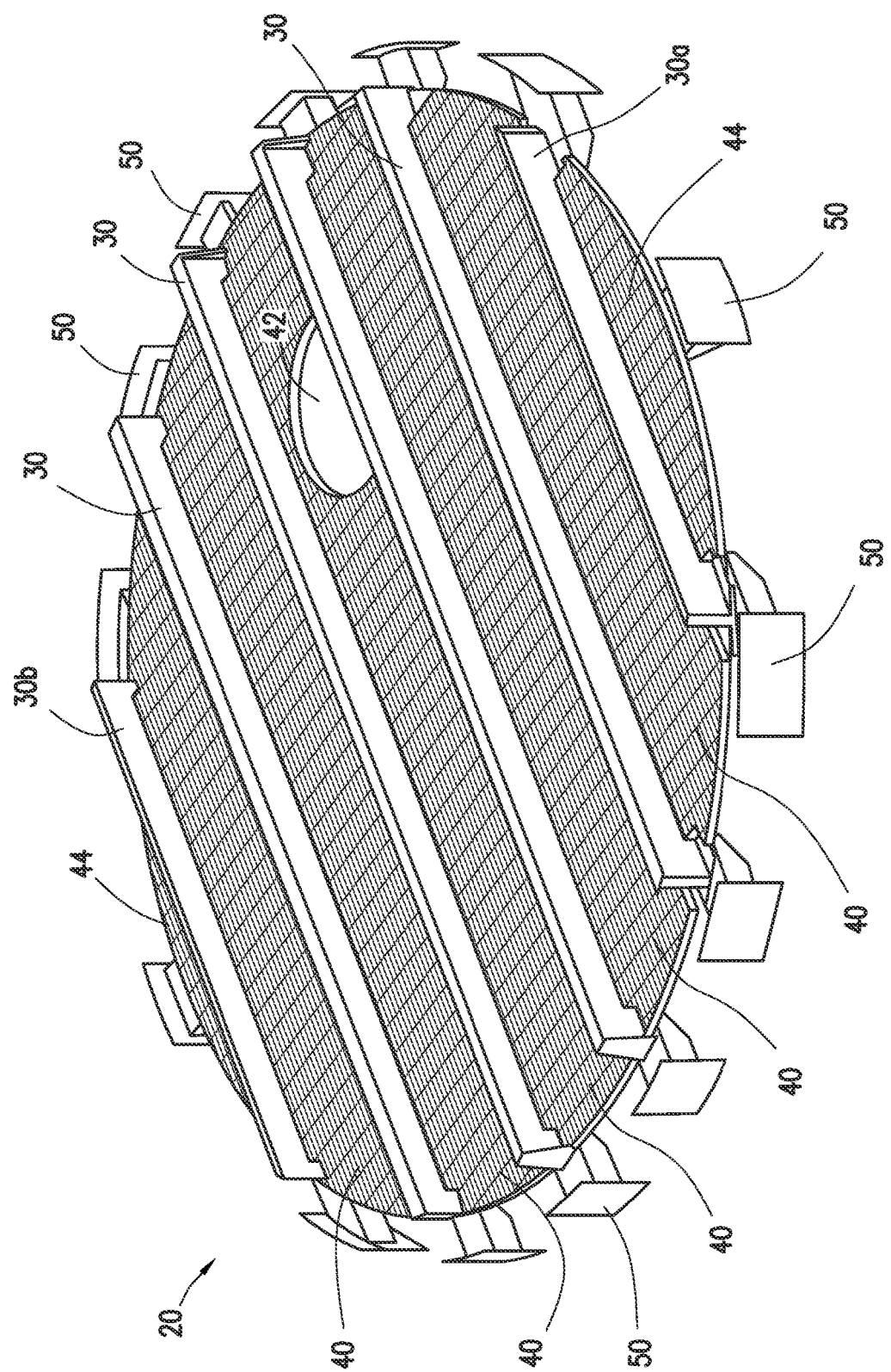
FIG. 2 is a perspective schematic view of a first embodiment of a grid assembly section of a fluid solids contacting device.

Referring to FIG. 1, a first embodiment of the fluid solids contacting device is illustrated. The device includes a shell, or vessel, 10 which encloses one or more grid assembly sections 20. Each grid assembly section 20 is formed from a plurality of horizontal chords 30 spaced horizontally apart from each other and a plurality of grid platforms 40 (as shown in FIG. 2) inserted between the horizontal chords. Each horizontal chord 30 comprises a structural member with sufficient mechanical strength to withstand fluidized forces in the vessel 10.

Figure 3:
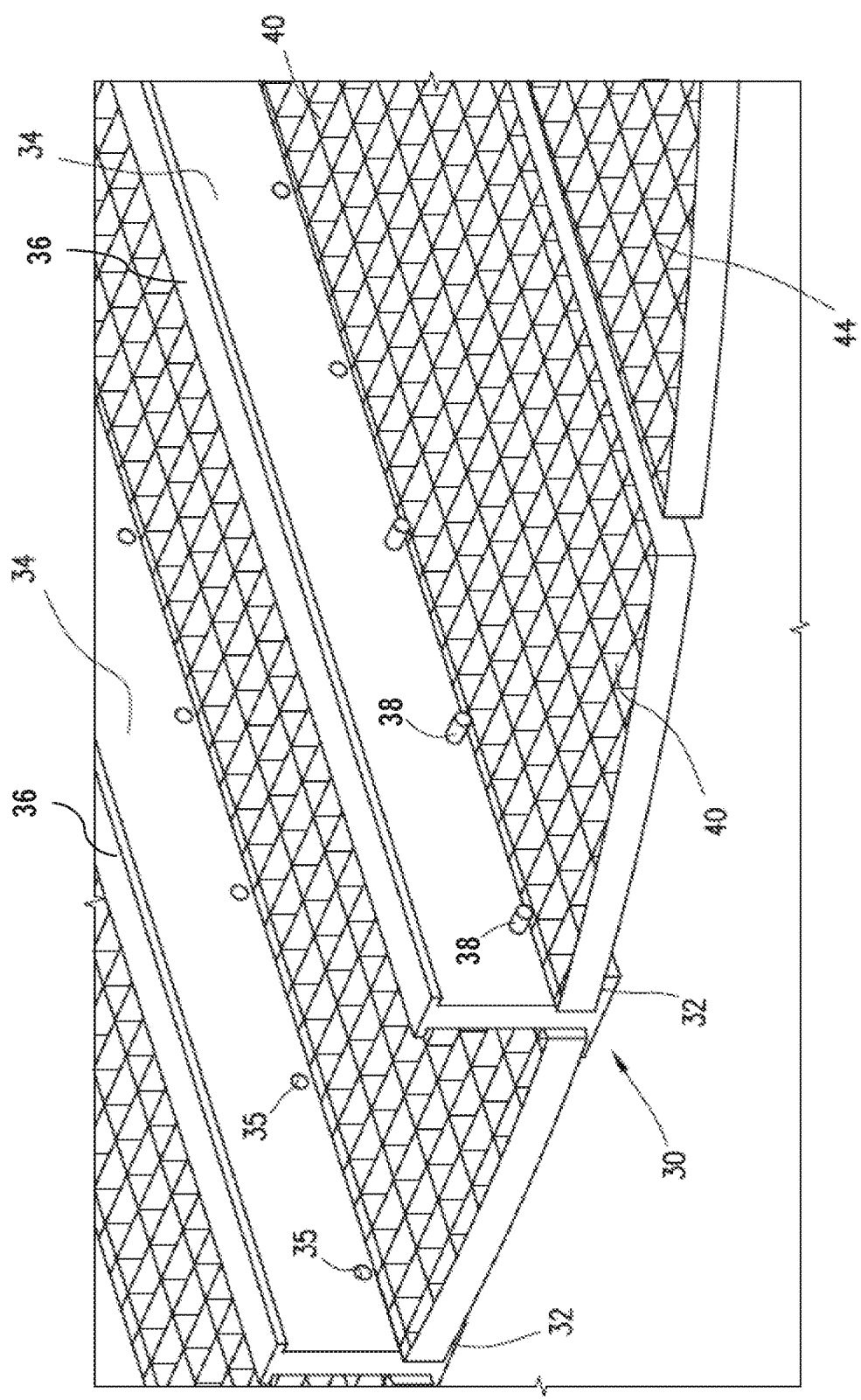
FIG. 3 is a perspective close up schematic view of a second embodiment of a grid assembly section of a fluid solids contacting device.

As shown in FIGS. 2 and 3, the horizontal chords 30 have a structural member with a substantially I-beam or inverted T-beam shape. The shape of the structural member is configured so that the grid platforms 40 may rest upon a part of the structural member. As shown in FIG. 3, the structural member comprises a bottom plate 32, a center plate 34 extending upwardly from a centerline of the bottom plate 32 and capped by a top plate 36 and wherein the grid platforms 40 may be supported on the bottom plates 32 and/or the top plates 36. While FIG. 3 illustrates a particular form for the horizontal chords 30, it will be understood that the horizontal chord may have any shape with the proviso that it supports or holds the grid platforms 40. For example, the horizontal chords 30 could be made of a flat structural member with sufficient strength to withstand fluidized forces in the vessel 10. As further shown in FIG. 3, the center plate 34 may optionally include openings 35 into which pegs 38 may be inserted such that the pegs 38 extend over the grid platforms 40 to prevent their upward movement. The opening and peg method is solely illustrative of a particular embodiment. Any method may be used to prevent lifting of the grid platforms 40. For example, clips, ties or similar fasteners may be used. Alternatively, structural components of the horizontal chords 30, such as overhanging lips, may be used to prevent upward lifting of the grid platform 40. The disclosure further provides the device 10 according to any embodiment disclosed herein except that the horizontal chord 30 further comprises an end cap (not shown) on one or both ends of the chord 30. The end caps may be configured to improve holding of the horizontal chord 30 on or within the chair against fluidized forces in the vessel and/or thermal or pressure induced expansion and/or contraction. The horizontal distance between the horizontal chords 30 are generally dependent on size and intended use of the vessel and strength of the horizontal chords. Such horizontal distance is determined, in a particular embodiment, by determining a distance a grid platform 40 can span and hold up to a 2 psi surge force.

Each grid assembly section further comprises a plurality of grid platforms 40. Each grid platform 40 spanning two horizontal chords 30 or between an outermost chord and a chair may comprises one or more sections. Grid platforms 40 may fill wholly or partially the spaces between the horizontal chords 30. The grid platforms may optionally be shaped to allow passage of other internal members of the vessel 10. For example, in FIG. 2, an opening 42 in a grid platform 40 would permit passage of another vessel internal such as a catalyst transfer line 17. The grid platforms 40 comprise any structure which forms a flow obstruction and is capable of breaking bubbles flowing in the vessel 10. Such structures include, subway grating, chevrons, packing, round bars, pipes, flat bars, angle iron, and the like. The disclosure further provides a device in accordance with any embodiment disclosed herein, except that the grid platform 40 comprises one or more of the group consisting of subway grating, chevrons, packing structures or combination of two or more thereof. As shown in FIG. 2, the grid assembly structure may optionally include one or two end grid platforms 44 which are held in place by the outermost horizontal chords 30a and 30b and a chair 50. Each grid platform 40 spanning two horizontal chords 30 or between an outermost chord and a chair may comprises one or more sections. As shown in FIG. 2, for example, a grid platform 40 may comprise three separate but abutting sections, 40a, 40b, and 40c. In those embodiments in which a grid platform comprises more than one section, the sections may, but need not, be attached to each other.

As further shown in FIG. 1, the vessel 10 may contain a plurality of grid assembly sections 20; specifically, four grid assembly sections shown in FIG. 1. In a particular embodiment, the number of grid assembly sections in the vessel 10 ranges from 1 to 20. All individual values and subranges from 1 to 20 are included and disclosed herein; for example, the number of grid assembly sections can range from a lower limit of 1, 5, 10, or 15 to an upper limit of 2, 6, 8, 12, 14 or 20.

Each of the grid assembly sections are spaced vertically from each other. The vertical spacing of the grid assembly sections may be uniform or variable throughout the vessel 10. As shown in FIG. 1, each grid assembly section are separated by substantially equal distances. The number of grid assembly sections 20 and the vertical distance between the grid assembly sections 20 may vary from several inches to several feet, depending on, inter alia, the particular use for the vessel 10, size of the vessel 10, operating pressure, physical characteristics of the solids being fluidized, and the superficial gas velocity in the vessel 10. The superficial gas velocity in the vessel 10 may range from 0.1 to 10 ft/s. All individual values from 0.1 to 10 ft/s are included and disclosed herein; for example, the superficial gas velocity in the vessel may range from a lower limit of 0.1, 2, 4, 6 or 8 ft/s to an upper limit of 0.5, 1, 3, 5, 7, 9 or 10 ft/s. For example, the superficial gas velocity in the vessel may range from 0.1 to 10 ft/s, or in the alternative, from 0.1 to 7.8 ft/s, or in the alternative, 0.5 to 8 ft/s, or in the alternative, from 1 to 7.7 ft/s. In a particular embodiment, the superficial gas velocity in the vessel is less than 8 ft/s. As used herein, "superficial velocity" is the gas velocity in the entire vessel and the term "slot velocity" is the gas velocity through grid platform openings, i.e., the gas velocity not blocked by the beams and solid parts of the grid platform. The slot velocity of the gas should range from 1 to 8 ft/s. Slot velocities higher than 8 ft/s can result in flooding and will not allow dense catalyst beds to form in the vessel.

Internals can be used that are capable of blocking 10% to 80% of the vessel open area. In particular embodiments, the horizontal cords may block 20-30% of the open area while the subway grating may block 10% to 40% of the remaining open area. A standard 1 inch by 4 inch grating with ¼" thick bars can block 30% of the open area.

The disclosure further provides a device in accordance with any embodiment disclosed herein except that the vessel is used as a reactor.

The disclosure further provides a device in accordance with any embodiment disclosed herein except that the vessel is used as a combustor.

The disclosure further provides a device in accordance with any embodiment disclosed herein except that the vessel is used as a catalyst conditioner.

The disclosure further provides a device in accordance with any embodiment disclosed herein except that the vessel is used as a catalyst stripper.

The disclosure further provides a device in accordance with any embodiment disclosed herein the device is a reactor or a combustor and exhibits co-current upflow conditions. Co-current upflow means that the average gas and solids flow are flowing upward although some solids may back mix.

The disclosure further provides a device in accordance with any embodiment disclosed herein the device is a catalyst conditioner or catalyst stripper and exhibits countercurrent flow conditions with the gas flowing upward and the solids flowing downward. Flowing refers to the average velocity of a particular stream and does not preclude backmixing. The disclosure further provides the fluid solids contacting device according to any embodiment described herein except that the device is used as a dehydrogenation reactor wherein a primary feedstock into the device is selected from the group consisting of ethane, propane, butane, n-butane, iso-butane, isobutene, n-butene, ethylbenzene, cumene, and any combination of two or more thereof.

Figure 4:
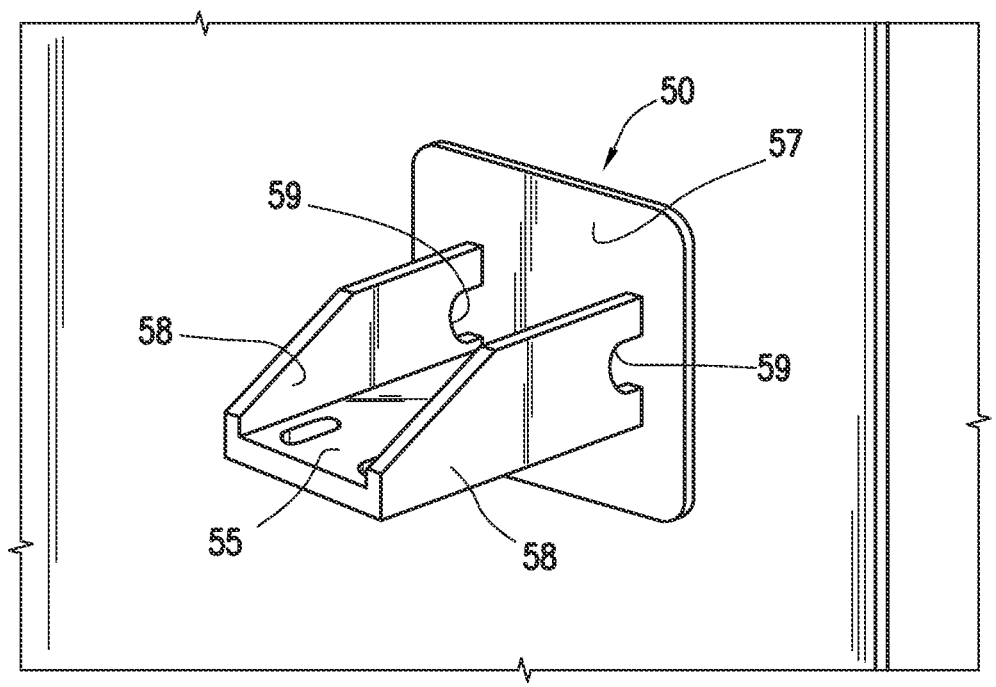
FIG. 4 is a schematic illustrating a first embodiment of the chairs used in the inventive device.

The grid assembly sections 20 are held in place within the vessel by the use of chairs 50 which are spaced around the interior surface 15 of the vessel 10. The chairs 50 are attached directly or indirectly to the interior surface 15 and provide a horizontal ledge 55 onto or into which the ends of the horizontal chords are placed. The placement of the chairs 50 is such that the chairs 50 support or hold the horizontal chords 30. FIG. 4 illustrates one embodiment of the chairs 50. As shown in FIG. 4, a ledge 55 is attached to a plate 57. The plate 57 may be directly attached to the interior surface 15 of the metal vessel or alternatively, may be attached to one or more interfaces (not shown), such as a compatible metal plate, which may be directly attached to the interior surface 15. Optionally, the chairs 50 may be wholly or partially wrapped, encased or coated with one or more refractory materials (not shown). As further shown in FIG. 4, the chair further includes two side rails 58 extending upward from either side of the ledge 55. The side rails 58 and the ledge 55 form a channel into which an end of a horizontal chord may sit. In one embodiment, the end of the horizontal chord rests within the channel such that it may move with thermal expansion and contraction during operation of the vessel. In an alternative embodiment, each horizontal chord 30 is bolted or otherwise attached to a chair 50 such that the beam may move with changes in temperature and/or pressure. Referring again to FIG. 4 it can be seen that each of the side rails 58 include optional notches to limit thermal transmission from the ledge 55 and side rails 58 onto the plate 57. While FIG. 4 illustrates one embodiment of a chair, other structures are included in the scope of the invention with the proviso that each chair is capable of supporting an end of a horizontal chord 30 while permitting thermal expansion and contraction. For example, in an alternative configuration, the end of a horizontal chord may be configured as a tunnel or tube which fits over a horizontal ledge of a chair without rails. Alternatively, the chair could be formed from a ledge, side rails and a top thereby forming a tunnel or tube into which an end of a horizontal chord could be placed.

As previously stated, in particular embodiments, the fluid solids contacting device may be used as a reactor, combustor, catalyst conditioner or catalyst stripper. That is, the fluid solids contacting device may be used under a wide range of conditions.

In a particular embodiment the fluid solids contacting device is used for dehydrogenation of hydrocarbons, fluidized catalytic cracking or methanol to olefins processes. In another embodiment the fluid solids contacting device is used for dehydrogenation of lower paraffins to form their corresponding olefins, or of lower olefins to form their corresponding di-olefins. In a particular embodiment the primary feedstock to the fluid solids contacting device is a C3, C4, and/or ethylbenzene hydrocarbon feed.

When used as a dehydrogentation reactor, the contacting a hydrocarbon feed and a catalyst feed comprising a catalyst meeting the requirements of a Geldart A or Geldart B classification in a fluidized dehydrogenation reactor, i.e., the fluid solids contacting device of the present invention, at a catalyst feed to hydrocarbon feed ratio of 5 to 100 on a weight to weight basis; wherein optionally the hydrocarbon feed and the catalyst feed have been preheated to a temperature of from about 400 degrees Celsius (° C.) to about 660° C.; in a dehydrogenation reactor wherein the average contact time between the hydrocarbon feed and the catalyst feed is from about 1 to about 10 seconds; and the temperature in the dehydrogenation reactor is maintained at a reaction temperature from about 550° C. to about 750° C.; and the pressure in the dehydrogenation reactor is maintained from about 41.4 kilopascals (kPa) to about 308.2 kPa (about 6.0 to about 44.7 pounds per square inch absolute, psia) at the outlet of the reactor In most embodiments of the invention, the reaction temperature is greater than 500° C. and preferably greater than 550° C. In particular embodiments the reaction temperature is from 500° C., preferably 550° C., more preferably 570° C., to 760° C. The average contact time should be sufficiently long to dehydrogenate acceptable amounts of the starting hydrocarbon feed, but not so long as to result in unacceptable amounts of by-products. While the required contact time is related to the specific feed, catalyst(s) and reaction temperature(s), in preferred embodiments of the invention the contact time within the dehydrogenation reactor is less than 60 seconds, preferably less than 10 seconds, more preferably less than 8 seconds, and still more preferably less than 7 seconds. Contact times may therefore range from about 0.5 or about 1 to about 10 seconds, preferably from about 0.5 or about 1 to about 8 seconds, and more preferably from about 0.5 or about 1 to about 7 seconds.

The average residence time of the catalyst within the reactor is preferably less than about 500 seconds, preferably from about 5 to about 240 seconds, more preferably from about 20 to about 150 seconds, and still more preferably from about 25 to about 100 seconds. Application of these times tends to decrease the amount of catalyst required for the process, enabling reduced catalyst inventories. Such inventories, in turn, provide the advantage of reducing operating and capital costs, in comparison with some prior art processes.

At the provided catalyst residence times and average contact times in the dehydrogenation reactor, the applied temperature of the reaction mixture, which may be supplied in major part by the hot fresh or regenerated catalyst, is desirably from about 500° C. to about 800° C., preferably from about 550° C. to about 760° C., and still more preferably from about 600° C. to about 760° C. Those skilled in the art will understand that the dehydrogenation reaction of the aforementioned compounds is inherently endothermic and that some flexibility within these temperature ranges may in some instances be obtained by appropriate modification of other variables according to the needs of a facility's overall process design.

Temperatures will also be affected by the type of dehydrogenation reactor used in the inventive process. A variety of types may be utilized, provided such offer fluidized contact between the starting hydrocarbon feed and the catalyst feed. Examples of suitable reactor types may include a co-current or countercurrent fluidized reactor, a riser reactor, a downer reactor, a fast fluidized bed reactor, a bubbling bed reactor, a turbulent reactor, or a combination thereof. In one preferred embodiment, the reactor is a combination of a fast fluidized bed or turbulent reactor in its lower portion, and a riser reactor in its upper section. In another embodiment a fast fluidized or turbulent reactor may be connected to a separate riser reactor via a frustum. The reactor may be, in certain embodiments, a hot wall reactor or a cold wall reactor, and in either case it may be refractory-lined. It may be manufactured of conventional materials used in fluid catalytic cracking (FCC) or petrochemical processing, such as, for example, stainless steel or carbon steel, and is desirably of a quality capable of withstanding the processing variables including temperature, pressure and flow rates. In particular embodiments, wherein the reactor is a fluidized reactor having co-current rising flow, the highest temperature in the dehydrogenation reactor will be found at its lower end and, as reaction proceeds and the catalyst and reaction mixture ascends, the temperature will decrease in a gradient toward the upper end of the reactor. See, for example, U.S. Pat. No. 8,669,406 (B2) the disclosure of which is incorporated herein by reference in its entirety. The dimensions of the reactor are generally dependent upon the process design of the applicable facility, and such will generally take into account the proposed capacity or throughput thereof, the weight hourly space velocity (WHSV), temperature, pressure, catalyst efficiency, and unit ratios of feed converted to products at a desired selectivity.

In more particular embodiments the reactor may comprise two definable sections, such that the lower section may operate in a manner that is or approaches isothermal, such as in a fast fluidized or turbulent upflow reactor, while the upper section may operate in more of a plug flow manner, such as in a riser reactor. For example, in the previously described particular embodiment, the dehydrogenation reactor may comprise a lower section operating as a fast fluidized or turbulent bed and the upper section operating as a riser reactor, with the result that the average catalyst and gas flow moves concurrently upward. As the term is used herein, "average" refers to the net flow, i.e., the total upward flow minus the retrograde or reverse flow, as is typical of the behavior of fluidized particles in general.

The applicable operating pressure of the dehydrogenation reactor is broad, enabling optimization based, in embodiments wherein the inventive process is applied in a retrofitted plant, upon applicable economics as allowed for by any existing equipment that will be used for the retrofit. This will be well within the general understanding of the skilled practitioner. In general the pressure may range from 6.0 to 44.7 pounds per square inch absolute (psia, about 41.4 kilopascals, kPa, to 308.2 kPa), but it is preferred for most embodiments including C3 and C4 dehydrogenation that a narrower selected range, from 15 to 35 psia, (about 103.4 kPa to about 241.3 kPa), be employed, more preferably from 15 to 30 psia (about 103.4 kPa to about 206.8 kPa), still more preferably from 17 to 28 psia (about 117.2 kPa to about 193.1 kPa), and most preferably from 19 to 25 psia (about 131.0 kPa to about 172.4 kPa).

The WHSV for the dehydrogenation process may conveniently range from about 0.1 pound (lb) to about 100 lb of hydrocarbon feed per hour (h) per lb of catalyst in the reactor (lb feed/h/lb catalyst). For example, where a reactor comprises a lower portion that operates as a fast fluidized or turbulent reactor and an upper portion that operates as a riser reactor, the superficial gas velocity may range therein from about 2 feet per second (ft/s, about 0.61 meters per second, m/s) to about 80 ft/s (about 24.38 m/s), preferably from about 3 ft/s (about 0.91 m/s) to 10 ft/s (about 3.05 m/s), in the lower portion of the reactor, and from 30 ft/s (about 9.14 m/s) to about 70 ft/s (about 21.31 m/s) in the upper portion of the reactor. In alternative but less preferred embodiments, a reactor configuration that is fully of a riser type may operate at a single high superficial gas velocity, for example, in some embodiments at least 30 ft/s (about 9.15 m/s) throughout.

In the dehydrogenation reactor the catalyst feed to hydrocarbon feed ratio ranges from about 2 to about 100 on a weight to weight (w/w) basis. In a particular embodiment for dehydrogenation of propane, the ratio ranges from about 5 to about 40; more preferably from about 10 to about 36; and most preferably from about 12 to about 24.

It is noted that, in embodiments such as in the two-part reactor described hereinabove, the catalyst flux is preferably from about 1 pound per square foot-second ($lb/ft^2$-s) (4.89 $kg/m^2$-s) to about 20 $lb/ft^2$-s (97.7 $kg/m^2$-s) in the lower portion of the reactor, and from about 10 $lb/ft^2$-s (48.9 $kg/m^2$-s) to about 200 $lb/ft^2$-s (489 $kg/m^2$-s) in the upper portion of the reactor. In a downer reactor, a catalyst flux of higher than about 200 $lb/ft^2$-s may be employed, but is generally not preferred. Those skilled in the art will be able to appropriately adjust catalyst flux based upon WHSV and ratio of catalyst feed to hydrocarbon feed.

When the fluid solids contacting device is used as a combustor, a portion of the at least partially deactivated catalyst is transferred to an embodiment of the fluid solids contacting device and the portion of the at least partially deactivated catalyst is heated to a temperature of from 500° C. to 850° C. to combust the coke deposited on the catalyst, using heat generated by the coke combustion itself and supplemental fuel the heating resulting in a heated, further deactivated catalyst (in the case of dehydrogentation but not when used in connection with fluid catalytic cracking or methanol to olefins operations).

For the case in which fluid solids contacting device is used as a combustor in an dehydrogenation process, the partially deactivated catalyst is heated to a temperature of at least 660° C. but no greater than 850° C., preferably from 700° C. to 770° C., and more preferably from 720° C. to 750° C. Again, as for the dehydrogenation reactor, it is preferred that the combustor, which serves as a part of the regeneration area and wherein the coke will be combusted (i.e., oxidized with an oxygen containing gas) to form $CO_2$, comprise a lower section operating as a fast fluidized, turbulent, or bubbling bed and an upper section operating as a riser. This enables the combustor to operate with an average catalyst and gas flow moving concurrently upward. In this configuration the internals are critical to break up the bubbles and promote fuel, air and catalyst mixing. Another possible configuration, designed instead to enable an average catalyst flow downward and an average gas flow upward, comprises a fast fluidized, turbulent, or bubbling bed. Regardless of configuration, heat for the regenerator's combustion comes from a combination of combustion of the deposited coke, i.e., the coke itself supplies heat as a result of the oxidation reaction, and combustion of a supplemental fuel for processes that don't produce enough coke to drive the reaction in the reactor. As the term is used herein, "supplemental" means fuel other than the coke itself.

The WHSV for the such process in the combustor may conveniently range from about 0.1 to about 100 lb of air+fuel feed per hour (h) per lb of catalyst in the combustor (lb feed/h/lb catalyst). For example, where a combustor comprises a lower portion that operates as a fast fluidized or turbulent reactor and an upper portion that operates as a riser reactor, the superficial gas velocity may range therein from about 1 feet per second (ft/s, about 0.3 meters per second, m/s) to about 80 ft/s (about 24.38 m/s), preferably from about 2 ft/s (about 0.61 m/s) to 10 ft/s (about 3.05 m/s), in the lower portion of the reactor, and from 20 ft/s (about 6.09 m/s) to about 70 ft/s (about 21.31 m/s) in the upper portion of the combustor. In alternative but less preferred embodiments, a combustor configuration that is fully of a riser type may operate at a single high superficial gas velocity, for example, in some embodiments at least 30 ft/s (about 9.15 m/s) throughout.

It is noted that, in embodiments such as in the two-part combustor described hereinabove, the catalyst flux is preferably from about 1 pound per square foot-second ($lb/ft^2$-s) (4.89 $kg/m^2$-s) to about 20 $lb/ft^2$-s (97.7 $kg/m^2$-s) in the lower portion of the combustor, and from about 10 $lb/ft^2$-s (48.9 $kg/m^2$-s) to about 200 $lb/ft^2$-s (489 $kg/m^2$-s) in the upper portion of the combustor. In a downer combustor, a catalyst flux of higher than about 200 $lb/ft^2$-s may be employed, but is generally not preferred. Those skilled in the art will be able to appropriately adjust catalyst flux based upon WHSV and ratio of catalyst feed to air/supplemental fuel feed.

Pressure in the combustor ranges from 15 to 50 psia and more preferably from 25 psia to 40 psia.

When the fluids solids contacting device is used as a catalyst conditioner, the heated, further deactivated catalyst is subjected to a conditioning step which comprises maintaining the heated, further deactivated catalyst at a temperature of at least 660° C. (for a dehydrogenation process) or of at least 500° C. (for an FCC or methanol to olefins process) while exposing the heated, further deactivated catalyst to a flow of an oxygen-containing gas for a period of time The conditioning also occurs within the regeneration area of the process and may be accomplished in a reactivation zone comprising, for example, a fast fluidized, turbulent, or bubbling bed. In a particularly preferred embodiment, the reactivation zone configuration enables an average catalyst flow downward and an average gas flow upward, i.e., flows corresponding to those of the combustor, but other configurations are also possible. This conditioning step in an olefin dehydrogenation process may comprise maintaining the heated, further deactivated catalyst at a temperature of at least 660° C., but no more than 850° C., preferably from 700° C. to 770° C., and more preferably from 720° C. to 750° C., while exposing it to a flow of an oxygen-containing gas. The conditioning is desirably carried out such that the catalyst has an average catalyst residence time in the oxygen-containing gas of more than two minutes. Optionally, the regenerated catalyst may be stripped, using a gas that does not contain more than 0.5 mole percent (mol %) oxygen, to remove oxygen-containing gas molecules residing between the catalyst particles and/or inside of the catalyst particles.

The superficial gas velocity in the inventive device when used as a catalyst conditioner may range between 0.05 to 4 ft/s, or in the alternative, from 0.05 to 2 ft/s, or in the alternative, from 2 to 4 ft/s, or in the alternative, from 0.1 to 1 ft/s, or in the alternative, from 0.2 to 0.5 ft/s.

The catalyst flux in the inventive device when used as a catalyst conditioner ranges between 0.1 to 20 lb/ft$^2$ sec, or in the alternative, from 0.1 to 10 lb/ft$^2$ sec, or in the alternative, from 10 to 20 lb/ft$^2$ sec, or in the alternative, from 0.5 to 5 lb/ft$^2$ sec.

The pressure in the inventive device when used as a catalyst conditioner ranges from 15 to 50 psia, or in the alternative, from 15 to 32 psia, or in the alternative, from 33 to 50 psia, or in the alternative, from 25 psia to 40 psia.

The fluid solids contacting device may also be used as a reactor stripper. In such application, the catalyst flux in the device ranges between 5 to 50 lb/ft$^2$ sec, or in the alternative, from 5 to 25 lb/ft$^2$ sec, or in the alternative, from 25 to 50 lb/ft$^2$ sec, or in the alternative, from 10 to 40 lb/ft$^2$ sec. The superficial gas velocity in the reactor stripper ranges from 0.1 to 4 ft/s, or in the alternative, from 0.1 to 2 ft/s, or in the alternative, from 2 to 4 ft/s, or in the alternative, from 0.2 to 1.5 ft/s. Pressure for reactor stripper ranges from 6.0 to about 44.7, or in the alternative, from 6 to 25 psia, or in the alternative, from 25 to 44.7 psia, or in the alternative, from 15 psia to 35 psia. The temperature in the reactor stripper ranges from 400 to 750° C., or in the alternative, from 400 to 575° C., or in the alternative, from 575 to 750° C., or in the alternative, from 450 to 650° C.

The present invention may be embodied in other forms without departing from the spirit and the essential attributes thereof, and, accordingly, reference should be made to the appended claims, rather than to the foregoing specification, as indicating the scope of the invention.

We claim:

1. A fluid solids contacting device comprising:
   a vessel;
   a first grid assembly section which comprises a plurality of horizontal chords spaced horizontally apart from each other and a plurality of grid platform(s) inserted between the horizontal chords;
   wherein each horizontal chord comprises a structural member with sufficient mechanical strength to withstand fluidized forces in the vessel and each grid platform is attached to one or more horizontal chords in a manner to prevent upward movement of the grid platform;
   a plurality of chairs attached directly or indirectly to an inside surface of the vessel and spaced circumferentially apart to support the structural member; and
   wherein each structural member is supported on one or more of the plurality of chairs, and wherein the structural member comprises a bottom plate, a center plate extending upwardly from a centerline of the bottom plate and capped by a top plate and wherein the grid platforms are supported on the bottom plates and/or the top plates.

2. The fluid solids contacting device according to claim 1, further comprising one or more additional grid assembly section(s) spaced vertically apart from each other and from the first grid assembly section.

3. The fluid solids contacting device according to claim 1, wherein the grid platforms comprise one or more of the group consisting of subway grating, chevrons, packing structures or any structure which forms a flow obstruction and is capable of breaking bubbles.

4. The fluid solids contacting device according to claim 1, where a gas slot velocity is less than 8 ft/s.

5. The fluid solids contacting device according to claim 1, wherein the device is a reactor, a combustor, a catalyst conditioner or a catalyst stripper.

6. The fluid solids contacting device according to claim 5, where the reactor, combustor, catalyst conditioner or catalyst stripper is used in a dehydrogenation process wherein one or more of the group consisting of ethane, propane, butane, n-butane, iso-butane, isobutene, n-butene, ethylbenzene, cumene, and any combination of two or more thereof are used as a primary feedstock.

7. The fluid solids contacting device according to claim 6, where the device is a reactor or a combustor and exhibits co-current upflow conditions.

8. The fluid solids contacting device according to claim 6, where the device is a catalyst conditioner or catalyst stripper and exhibits countercurrent flow conditions.

* * * * *